US006678651B2

(12) United States Patent
Gao

(10) Patent No.: US 6,678,651 B2
(45) Date of Patent: Jan. 13, 2004

(54) SHORT-TERM ENHANCEMENT IN CELP SPEECH CODING

(75) Inventor: Yang Gao, Mission Viejo, CA (US)

(73) Assignee: Mindspeed Technologies, Inc., Newport Beach, CA (US)

( * ) Notice: Subject to any disclaimer, the term of this patent is extended or adjusted under 35 U.S.C. 154(b) by 374 days.

(21) Appl. No.: 09/771,293

(22) Filed: Jan. 25, 2001

(65) Prior Publication Data

US 2003/0004710 A1 Jan. 2, 2003

Related U.S. Application Data

(60) Provisional application No. 60/232,939, filed on Sep. 15, 2000.

(51) Int. Cl.[7] .......................... G10L 19/14; G10L 19/04; G10L 13/02
(52) U.S. Cl. ........................ 704/219; 704/211; 704/262
(58) Field of Search ................................ 704/219, 220, 704/222, 201, 204, 209, 211, 262

(56) References Cited

U.S. PATENT DOCUMENTS

| | | | | |
|---|---|---|---|---|
| 5,125,030 A | * | 6/1992 | Nomura et al. | 704/222 |
| 5,265,190 A | * | 11/1993 | Yip et al. | 704/219 |
| 5,664,055 A | * | 9/1997 | Kroon | 704/219 |
| 5,699,485 A | * | 12/1997 | Shoham | 704/219 |
| 5,793,930 A | * | 8/1998 | Moulsley | 704/219 |
| 5,845,244 A | * | 12/1998 | Proust | 704/219 |
| 5,884,251 A | * | 3/1999 | Kim et al. | 704/219 |
| 6,029,125 A | * | 2/2000 | Hagen et al. | 704/201 |
| 6,041,297 A | * | 3/2000 | Goldberg | 704/219 |
| 6,058,359 A | * | 5/2000 | Hagen et al. | 704/219 |

FOREIGN PATENT DOCUMENTS

| | | | | |
|---|---|---|---|---|
| JP | 08-146998 | * | 6/1996 | G10L/9/14 |
| JP | 10-020891 | * | 1/1998 | G10L/9/14 |
| JP | 10-105197 | * | 4/1998 | G10L/9/14 |

OTHER PUBLICATIONS

Vaidyanathan ("Orthonormal and Bi–orthonormal Filter Banks as Convolvers, and Convolutional Coding Gain", IEEE Transactions on Signal Processing, vol. 41 issue 6, pp.: 2110–2130, Jun. 1993).*
Gao et al ("eX–CELP: a Speech Coding Paradigm", 2001 IEEE International Conference on Acoustics, Speech, and Signal Processing Proceedings, May 2001).*
Mohammadi et al ("Low Cost Vector Quantization Methods For Spectral Coding In Low Rate Speech Coders", International Conference on Acoustics, Speech, and Signal Processing, May 1995).*
Xydeas ("Modern Developments In Speech Coding", IEEE Colloquium on Spectral Estimation Techniques for Speech Processing, Feb. 1989.*
Woodard et al ("Improvements to the Analysis–by–Synthesis Loop in CELP", International Conference on Radio Receivers and Associated Systems.*
WO 94 25959 A (Unisearch Ltd ;SEN Dipanjan (AU); Holmes Warwich–Harvey (AU) Nov. 10, 1994, figure 1A p. 1, line 10–line 16.

* cited by examiner

Primary Examiner—Doris H. To
Assistant Examiner—Daniel A. Nolan
(74) Attorney, Agent, or Firm—Farjami & Farjami LLP

(57) ABSTRACT

A speech-coding device includes a fixed codebook, an adaptive codebook, a short-term enhancement circuit, and a summing circuit. The short-term enhancement circuit connects an output of the fixed codebook to a summing circuit. The summing circuit adds an adaptive codebook contribution to a fixed codebook contribution. The short-term enhancement circuit can also be connected to a synthesis filter to emphasize the spectral formants in an encoder and a decoder.

32 Claims, 9 Drawing Sheets

SHORT-TERM ENHANCEMENT IN CELP SPEECH CODING

CROSS REFERENCE TO RELATED APPLICATIONS

This application claims the benefit of provisional application serial No. 60/232,939 filed on Sep. 15, 2000. The following co-pending and commonly assigned U.S. patent applications have been filed on the same day as the provisional application. All of these applications relate to and further describe other aspects of the embodiments disclosed in this application and are incorporated by reference in their entirety.

U.S. patent application Ser. No. 09/663,242, "SELECTABLE MODE VOCODER SYSTEM," filed on Sep. 15, 2000.

U.S. patent application Ser. No. 09/755,441, "INJECTING HIGH FREQUENCY NOISE INTO PULSE EXCITATION FOR LOW BIT RATE CELP," filed on Sep. 15, 2000.

U.S. patent application Ser. No. 09/761,029, "SYSTEM OF DYNAMIC PULSE POSITION TRACKS FOR PULSE-LIKE EXCITATION IN SPEECH CODING," filed on Sep. 15, 2000.

U.S. patent application Ser. No. 09/782,791, "SPEECH CODING SYSTEM WITH TIME-DOMAIN NOISE ATTENUATION," filed on Sep. 15, 2000.

U.S. patent application Ser. No. 09/761,033, "SYSTEM FOR AN ADAPTIVE EXCITATION PATTERN FOR SPEECH CODING," filed on Sep. 15, 2000.

U.S. patent application Ser. No. 09/782,383, "SYSTEM FOR ENCODING SPEECH INFORMATION USING AN ADAPTIVE CODEBOOK WITH DIFFERENT RESOLUTION LEVVLS," filed on Sep. 15, 2000.

U.S. patent application Ser. No. 09/663,837, "CODEBOOK TABLES FOR ENCODING AND DECODING," filed on Sep. 15, 2000.

U.S. patent application Ser. No. 09/662,828, "BITSTREAM PROTOCOL FOR TRANSMISSION OF ENCODED VOICE SIGNALS," filed on Sep. 15, 2000.

U.S. patent application Ser. No. 09/781,735, "SYSTEM FOR FILTERING SPECTRAL CONTENT OF A SIGNAL FOR SPEECH ENCODING," filed on Sep. 15, 2000.

U.S. patent application Ser. No. 09/663,734, "SYSTEM OF ENCODING AND DECODING SPEECH SIGNALS," filed on Sep. 15, 2000.

U.S. patent application Ser. No. 09/663,002, "SYSTEM FOR SPEECH ENCODING HAVING AN ADAPTIVE FRAME ARRANGEMENT," filed on Sep. 15, 2000.

U.S. patent application Ser. No. 09/940,904, "SYSTEM FOR IMPROVED USE OF PITCH ENHANCEMENT WITH SUB CODEBOOKS," filed on Sep. 15, 2000.

BACKGROUND OF THE INVENTION

1. Technical Field

This invention relates to speech coding, and more particularly, to a system that enhances the perceptual quality of digital processed speech.

2. Related Art

Speech synthesis is a complex process that often requires the transformation of voiced and unvoiced sounds into digital signals. To model sounds, sounds are sampled and encoded into a discrete sequence. The number of bits used to represent the sound can determine the perceptual quality of synthesized sound or speech. A poor quality replica can drown out voices with noise, lose clarity, or fail to capture the inflections, tone, pitch, or co-articulations that can create adjacent sounds.

In one technique of speech synthesis known as Code Excited Linear Predictive Coding (CELP), a sound track is sampled into a discrete waveform before being digitally processed. The discrete waveform is then analyzed according to certain select criteria. Criteria such as the degree of noise content and the degree of voice content can be used to model speech through linear functions in real and in delayed time. These linear functions can capture information and predict future waveforms.

The CELP coder structure can produce high quality reconstructed speech. However, coder quality can drop quickly when the coder's bit rate is reduced. To maintain a high coder quality at a low bit rate, such as 4 Kbps, additional approaches must be explored. This invention is directed to providing an efficient coding system of voiced speech that accurately encodes and decodes the perceptually important features of voiced speech.

SUMMARY

This invention is a system that enhances the perceptual quality of reconstructed speech. The system adds short-term enhancements to the spectral envelope of coded voice segments. The system includes a fixed codebook, an adaptive codebook, an enhancement circuit, and a summing circuit. The enhancement circuit interconnects an output of the fixed codebook to a summing circuit. The summing circuit adds an adaptive codebook contribution to a fixed codebook contribution. In another aspect, the enhancement circuit may be connected directly to a synthesis filter.

Other systems, methods, features, and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The components in the figures are not necessarily to scale, emphasis instead being placed upon illustrating the principles of the invention. Moreover, in the figures, like reference numerals designate corresponding parts throughout the different views.

Figure 4:
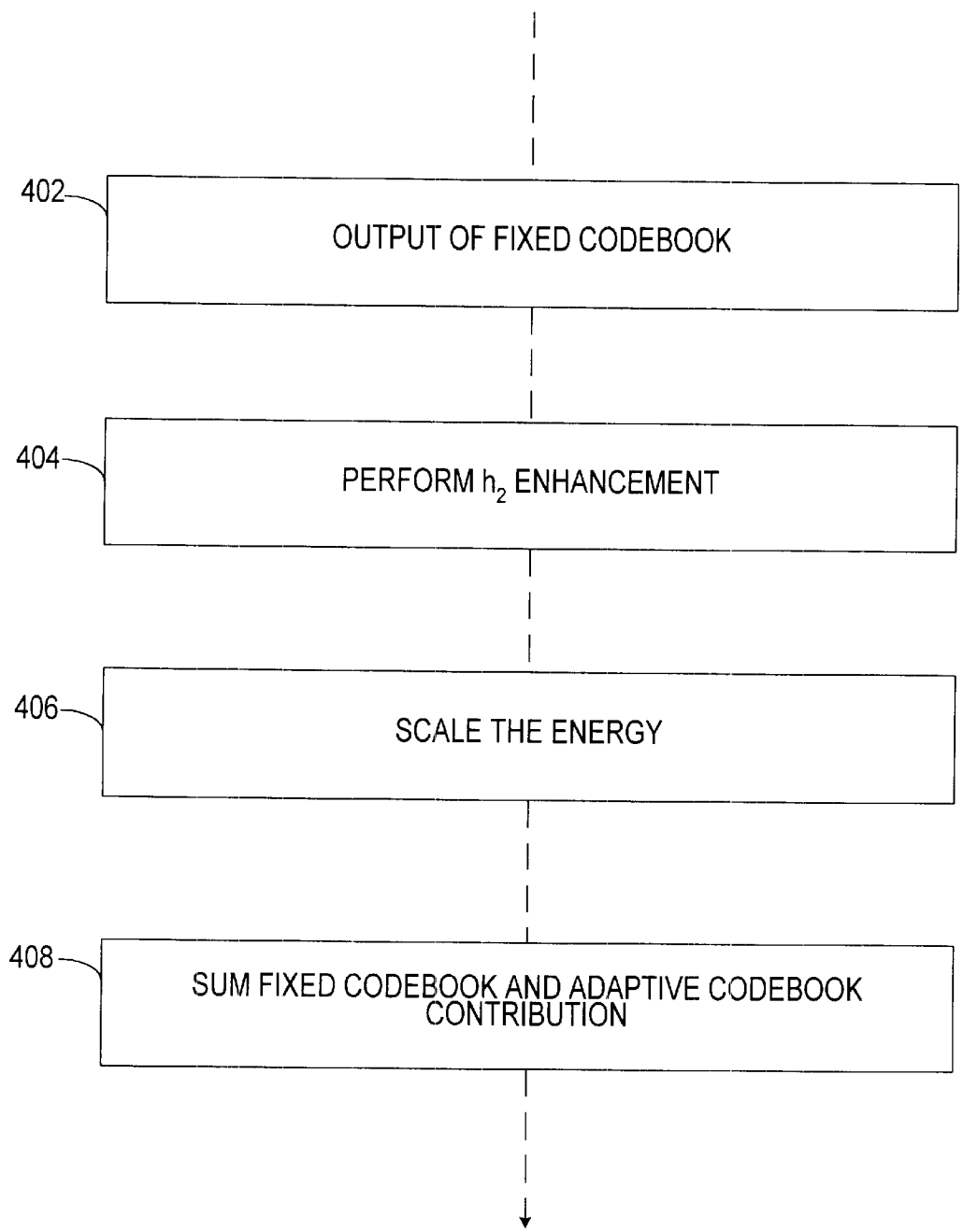
FIG. 4 is a flow diagram of an enhancement of FIG. 1.

The dashed lines drawn in FIGS. 1, 6, 8, and 9 represent direct and indirect connections. For example, the fixed codebook 102 of FIG. 1 may be directly or indirectly connected to other circuit components including circuits, devices, etc. The fixed codebook 102 can also include one or more subcodebooks as illustrated in FIG. 2. Similarly, the dashed lines of FIG. 4 illustrate that other functions can occur before or after each illustrated step.

DETAILED DESCRIPTION

Long-term enhancements to codebook excitations can improve the perceptual quality of reconstructed speech. Perceptual coders may add selective enhancements to the fine spectral structure that represents the long-term correlation of coded voiced segments. These enhancements, however, are not used to enhance the spectral envelope that represents the short-term correlation of coded voice segments. The addition of a short-term enhancement brings back some quality loses that can be caused by bandwidth expansion used in a Linear Prediction Coding (LPC) parameter quantization. A bandwidth expansion moves synthesis filter poles away from the unit circle.

Figure 1:
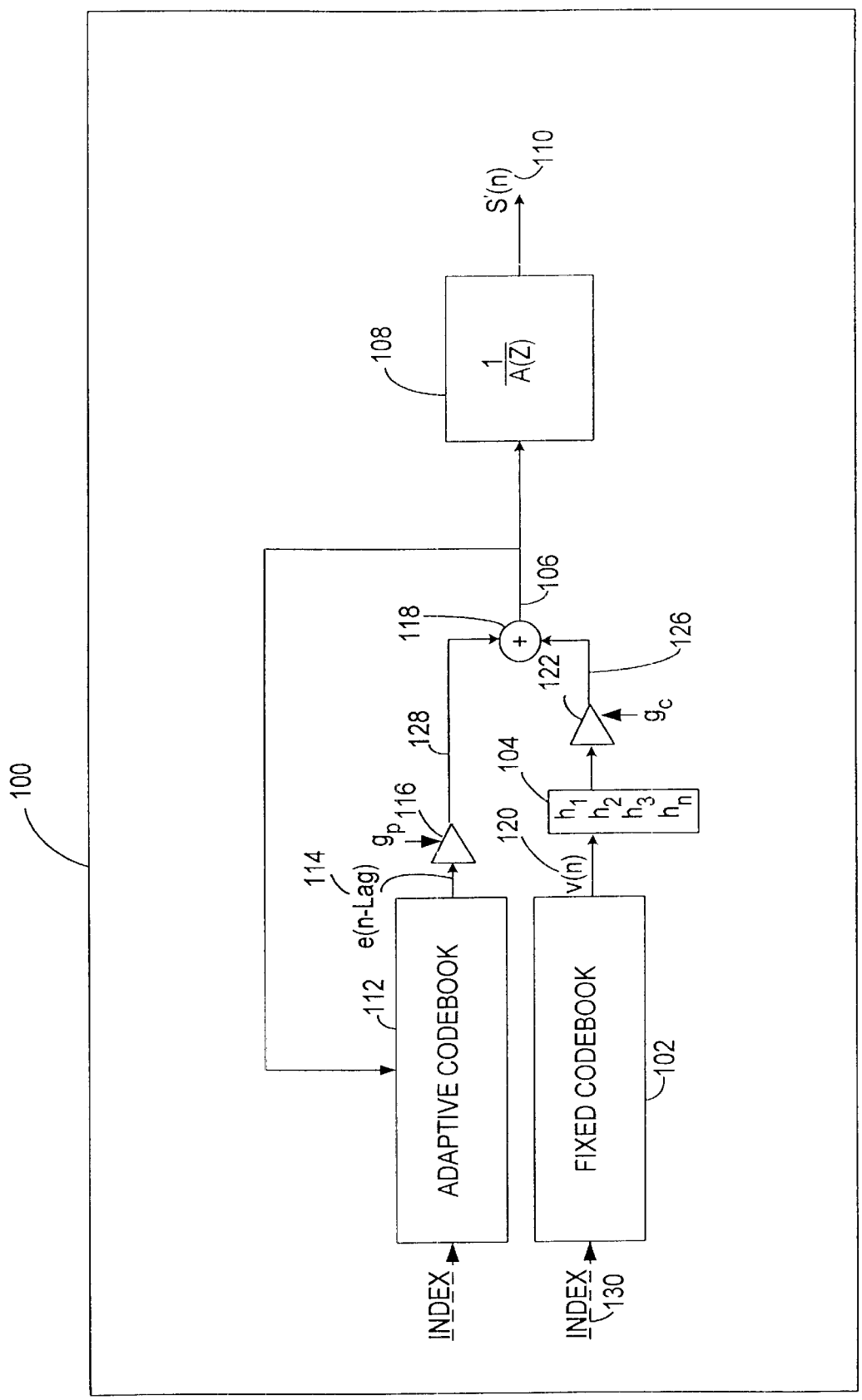
FIG. 1 is a partial block diagram of a speech communication system incorporated in a variant of a Code Excited Linear Prediction System (CELPS) known as the eXtended Code Excited Linear Prediction System (eX-CELPS).
Figure 2:
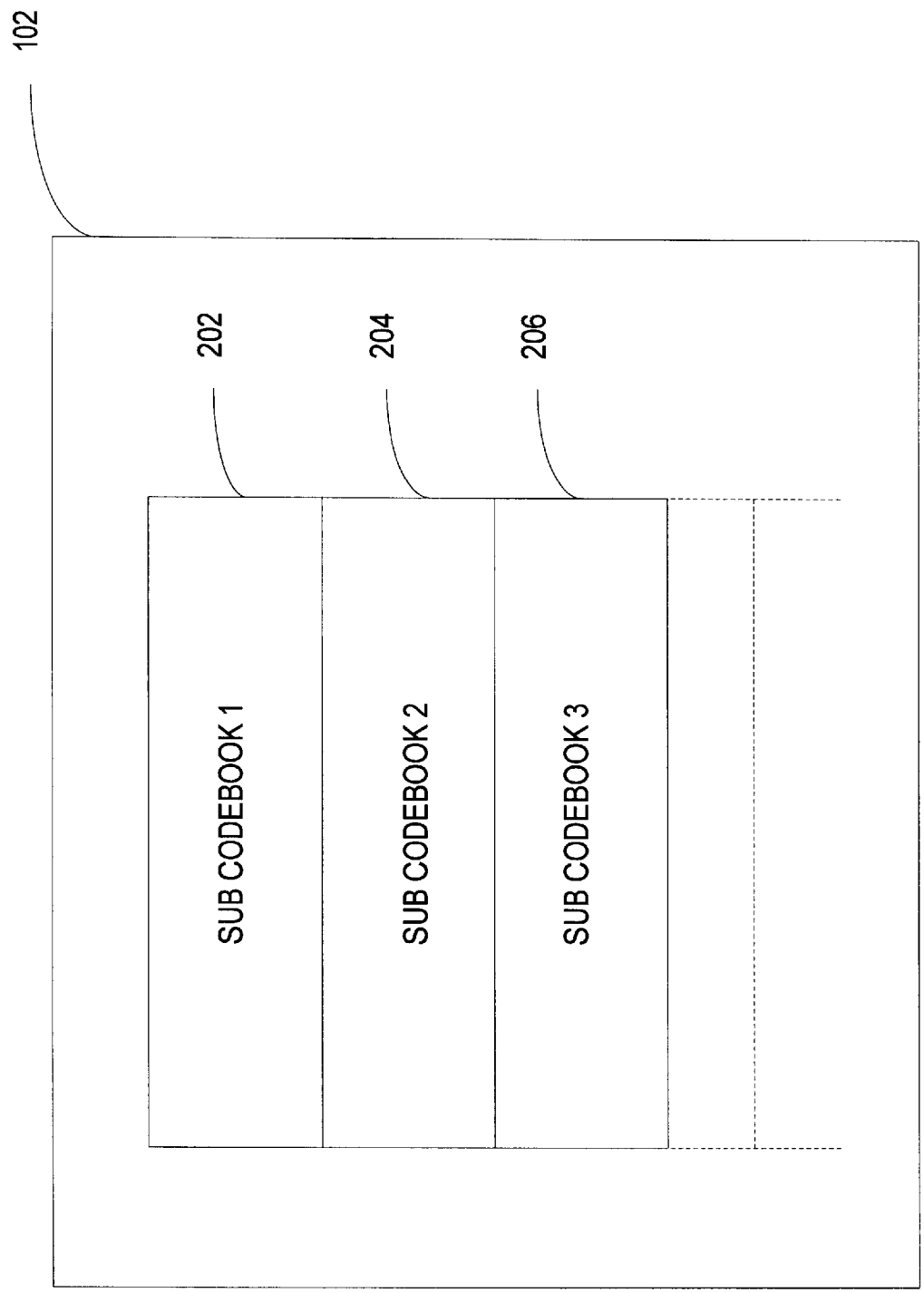
FIG. 2 illustrates a fixed codebook of FIG. 1.

FIG. 1 is a partial block diagram of a speech coding or speech communication system 100 incorporated in a variant of a Code Excited Linear Prediction System (CELPS) known as the eXtended Code Excited Linear Prediction System (eX-CELPS). Conceptually, eX-CELPS achieves toll quality at a low bit rate by emphasizing the perceptually important features of a sampled input signal (i.e., a voiced speech signal) while de-emphasizing the auditory features that are not perceived by a listener. Using a process of linear predictions, this embodiment can represent any speech sample. The short-term prediction of speech s at an instant n can be approximated by Equation 1:

$$s(n) \approx a_1 s(n-1) + a_2 s(n-2) + \ldots + a_p s(n-p) \quad \text{(Equation 1)}$$

where $a_1, a_2, \ldots a_p$ are Linear Prediction Coding coefficients (LPC coefficients) and p is the Linear Prediction Coding order. The difference between the speech sample and the predicted speech sample is called the prediction residual r(n) that has a similar level of periodicity as the speech signal s(n). The LPC residual r(n) can be expressed as:

$$r(n) = s(n) - a_1 s(n-1) - a_2 s(n-2) - \ldots - a_p s(n-p) \quad \text{(Equation 2)}$$

and can be re-written as:

$$s(n) = r(n) + a_1 s(n-1) + a_2 s(n-2) + \ldots + a_p s(n-p) \quad \text{(Equation 3)}$$

A closer examination of Equation 3 reveals that a current speech sample can be broken down into a predictive portion $a_1 s(n-1) + a_2 s(n-2) + \ldots + a_p s(n-p)$ and the LPC residual r(n). The Long Term Prediction residual (LTP residual) $r_2(n)$ is defined through the LPC residual r(n) and an adaptive codebook pitch prediction signal $g_p e(n-Lag)$ 128.

$$r_2(n) = r(n) - g_p e(n-Lag) \quad \text{(Equation 4)}$$

It is the filtering of the excitation signal e(n) 106 by a synthesizer or a synthesis filter 108 that produces the reconstructed speech signal s'(n) 110. The Lag is a measure of the pitch delay that is preferably the true pitch period. Thus, the excitation signal e at an instant n 106 can be expressed as:

$$e(n) = g_c v(n) + g_p e(n-Lag) \quad \text{(Equation 5)}$$

where v(n) 120 is the quantized output of the fixed codebook 102 and the adaptive codebook pitch prediction e(n−Lag) 114 is the output of the adaptive codebook 112.

Thus, to accurately reproduce voiced and unvoiced speech segments, the excitation signal e(n) 106 is created through a linear combination of the outputs from an adaptive codebook 112 and a fixed codebook 102. It must be emphasized that codebooks 102 and 112 should be interpreted in a very broad sense to include single and multiple sub codebooks.

The adaptive codebook 112 generates signals that represent the periodicity of the speech signal s(n). In this embodiment, the content of the adaptive codebook 112 is formed from previously reconstructed excitations signals e(n) 106. These signals repeat the content of a selectable range of previously sampled signals that lie within adjacent subframes. The content is stored in memory. Due to the high-degree of correlation that exists between the current and previous adjacent subframes, the adaptive codebook 112 tracks signals through selected adjacent subframes and then uses these previously sampled signals to generate the entire or a portion of the current excitation signal e(n) 106.

The second codebook used to generate the entire or a portion of the excitation signal e(n) 106 is the fixed codebook 102. The fixed codebook 102 primarily contributes the non-predictable or non-periodic portion of the excitation signal e(n) 106. This contribution improves the approximation of the speech signal s(n) when the adaptive codebook 112 cannot effectively model non-periodic signals. When noise-like structures or non-periodic signals exist in a sound track because of rapid frequency variations in voiced speech or because transitory noise-like signals mask voiced speech, for example, the fixed codebook 102 produces an approximation of these non-periodic signals that cannot be captured by the adaptive codebook 112.

The overall objective of the selection of codebook entries in this embodiment is to create the best excitations that approximate the perceptually important features of a speech segment. To improve performance, a modular codebook structure is used in this embodiment that structures the codebooks into multiple sub codebooks. Preferably, the fixed codebook 102 is comprised of at least three sub codebooks 202–206 as illustrated in FIG. 2. Two of the fixed sub codebooks are pulse codebooks 202 and 204 such as a 2-pulse sub codebook and a 3-pulse sub codebook. The third codebook 206 is a Gaussian codebook or a higher-pulse sub codebook. Preferably, the level of coding further refines the codebooks, particularly defining the number of entries for a given sub codebook. Further details of the codebooks are described in the co-pending patent application entitled: "System of Encoding and Decoding Speech Signals" by Yang Gao, Adil Beyassine, Jes Thyssen, Eyal Shlomot, and Huan-yu Su that is incorporated by reference.

Following a search of the fixed sub codebooks that yields the best output signals, some enhancements $h_1, h_2, h_3, \ldots h_n$ 104 are filtered or convoluted with the outputs of the codebooks to enhance the perceptual quality of the modeled signal. These enhancements preferably track select aspects of the speech segment and are calculated from subframe to subframe. An enhancement $h_2$ is introduced by filtering or convolving the output of the fixed codebook.

Figure 3:
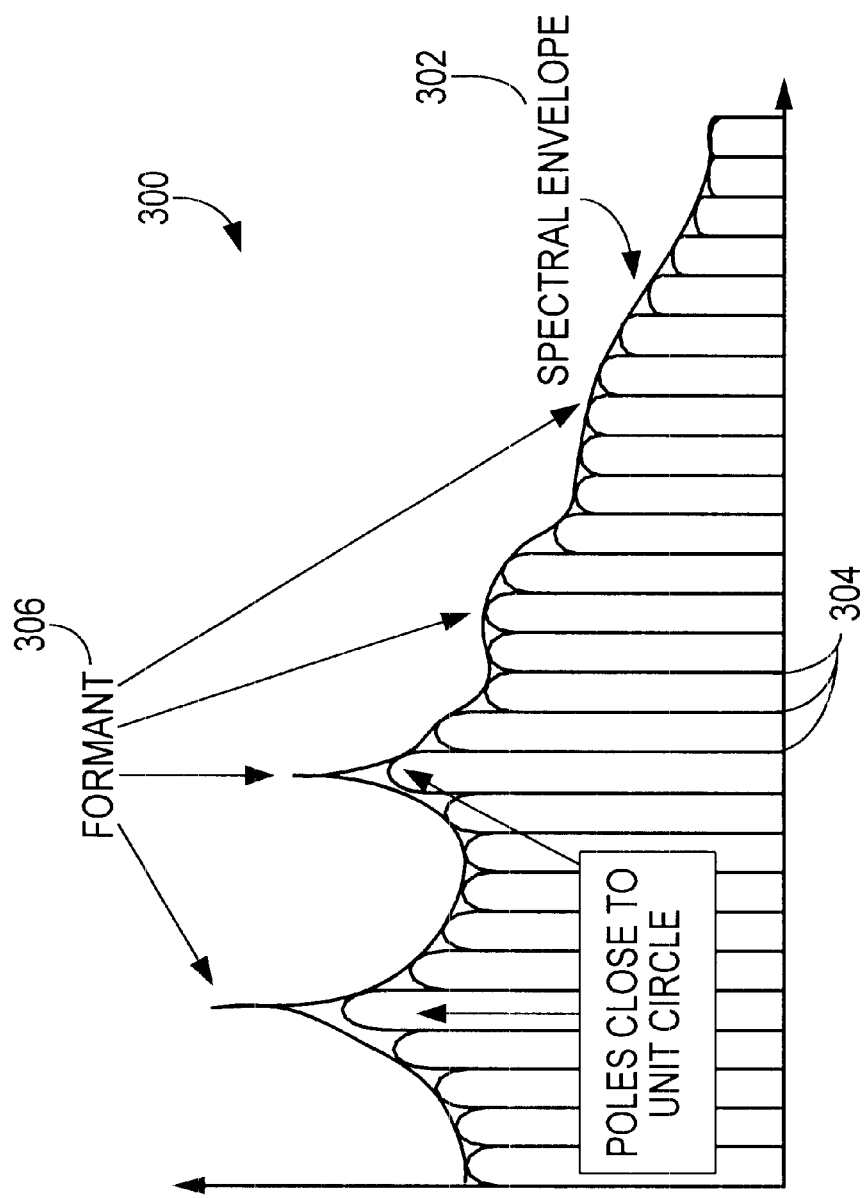
FIG. 3 illustrates a spectral envelope and a fine spectral structure of a speech segment.

As shown in FIG. 3, a sound track can be characterized by its properties in the power spectrum 300. In the power spectral domain, the power spectral envelope or pure LPC spectrum 302 corresponds to the "short-term" time domain correlations and the underlying fine structure 304 corresponds to the "long-term" time domain correlations.

Figure 7:
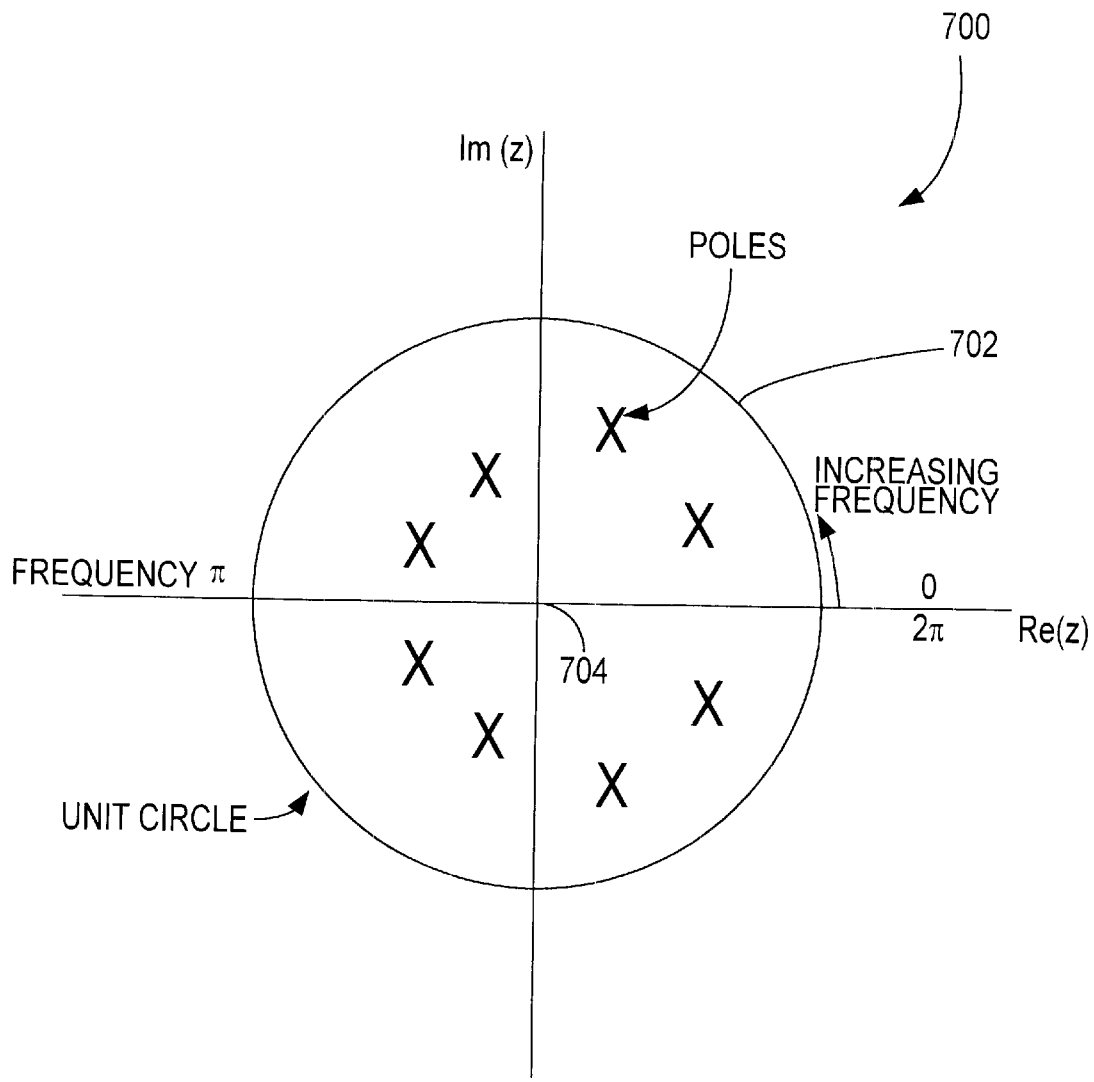
FIG. 7 illustrates an exemplary z-plane.

Samples of both the spectral envelope 302 and fine structure 304, in part, define the LPC coefficients $a_1, a_2, \ldots a_p$. Preferably, an autocorrelation method estimates the LPC coefficients although other methods that minimize prediction error for data sequences may also be used. When an autocorrelation method is used, the synthesis filter 108 is stable. In practical terms this means that the poles of the synthesis filter represented by the LPC coefficients lie within the unit circle 702 of the z-plane 700 shown in FIG. 7.

Figure 6:
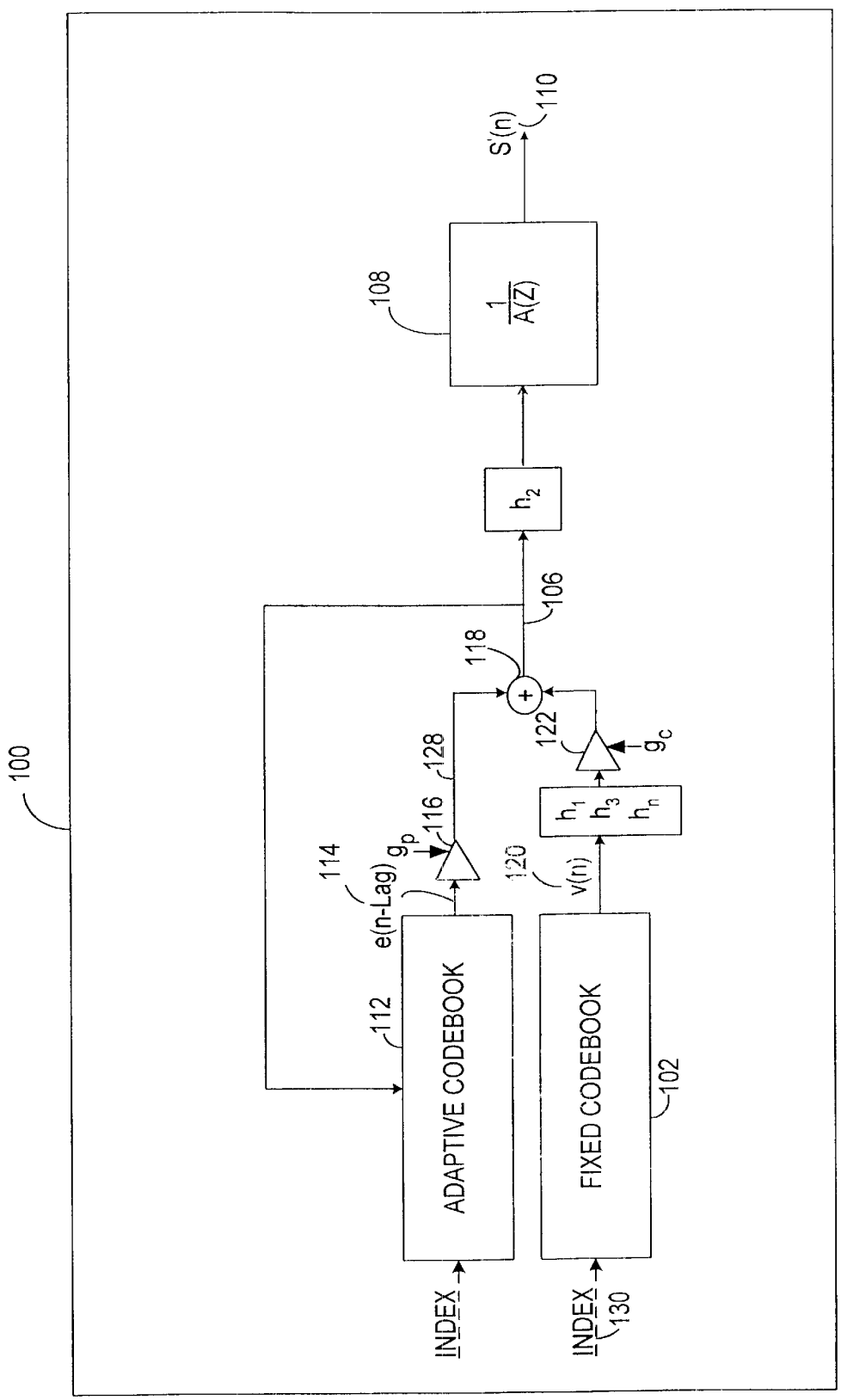
FIG. 6 is a block diagram of an alternative embodiment of the invention.

Before transmitting LPC coefficients, the LPC coefficients are subject to a quantization. Quantization can create an unstable synthesis filter 108 because small changes in the LPC coefficients can lead to a large change in the power spectrum 300. Accordingly, a bandwidth expansion may be used before the LPC quantization to make the formant structure less sharp by moving the poles of the bandwidth filter away from the circumference or toward the origin of the unit circle 702 in the z-plane 700. As shown in FIGS. 1 and 6, a short-term enhancement $h_2$ may be connected to an output of a fixed codebook 102 or to an output of a summing circuit 118. Preferably, the short-term enhancement $h_2$ occurs after the LPC quantization so that the short-term enhancement $h_2$ recovers some of the quality losses that can be caused by the bandwidth expansion. In practice, the short-term enhancement $h_2$ makes the combined spectral envelope sharper without affecting the stability of the synthesis filter 108 by moving the poles of the $h_2$ enhancement toward the circumference or away from the origin of the unit circle 702 in the z-plane 702.

As shown in FIG. 1, the vector v(n) 120 is selected by a fixed codebook index 130. The vector v(n) 120 is filtered or convolved by enhancement $h_2$ and then scaled by a scalar or a scaling circuit $g_c$, 122. Preferably, the enhancement $h_2$ is a spectral filter that emphasizes the formant structure 306 of the spectral envelope 302 shown in FIG. 3. In this embodiment, the spectral filter is defined by the transfer function $H_2(z)=1/A\ (z/\alpha)$ where $\alpha$ is preferably a small value. $\alpha$, for example, can be less than 0.1. The output of the spectral filter $H_2(z)$ V(z) 126 is then combined with the scaled pitch prediction $g_p e(n-Lag)$ 128 (generated by application of scalar $g_p$ 116 to predicted pitch e(n–Lag) 114) at a summing point by a summing circuit 118 to create the excitation signal e(n) 106.

$$e(n)=g_c \cdot h_2(n)*v(n)+g_p e(n-Lag) \qquad \text{(Equation 6)}$$

To reconstruct the peaks 306 of the LPC spectrum 302 of FIG. 3, the filter coefficients are preferably calculated through an expansion device. Preferably, the expansion device replaces the LPC coefficients $a_1, a_2, \ldots a_p$ with scaled coefficients $\gamma^1 a_1, \gamma^2 a_2, \ldots \gamma^p a_p$. The replacement of $a_p$ with $\gamma^p a_p$ is equivalent to scaling up the radii of all poles of the synthesis filter 108 by a factor of $\gamma$. This results in the creation of sharp pitch harmonic peaks that approximate the pitch harmonic peaks 306 of the pure LPC spectrum 302.

FIG. 4 is a flow diagram of the $h_2$ enhancement that can filter the excitation output of any codebook to enhance the perceptual quality of a reconstructed speech signal s'(n). At step 402, the fixed codebook index 130 is calculated and an output of the fixed codebook 102 is generated. The calculated index 130 of the fixed codebook 102 preferably results in the smallest difference between the original speech signal s(n) and the reconstructed s'(n) speech signal 110. At step 404, the vector v(n) 120 is filtered by the $h_2$ enhancement which emphasizes the sharp peaks 306 of the LPC spectrum 302. At step 406, an adaptive scaling factor $g_c$ is used to amplify or attenuate the fixed codebook contribution vector v(n) 120 to the excitation signal e(n) 106. At step 408, the excitation signal e(n) 106 is constructed from the adaptive 112 and the fixed codebook 102 contributions. The adaptive contribution, which is the scaled pitch prediction $g_p e(n-Lag)$ 128, is added to the fixed codebook contribution which is the enhanced scaled vector $H_2(z)V(z)$ 126.

Figure 5:
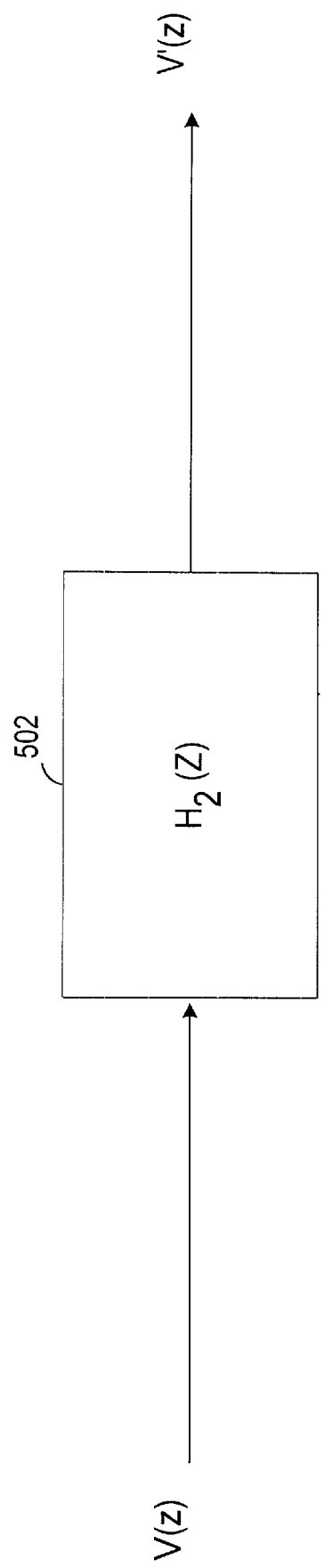
FIG. 5 illustrates a discrete implementation of the enhancement of FIG. 1.

Of course, the enhancement $h_2$ also can be implemented in the discrete-domain through a convolver having at least two ports or means 502 comprising a digital controller (i.e., a digital signal processor), one or more enhancement circuits, one or more digital filters, or other discrete circuitry. These implementations illustrated in FIG. 5 can be described as follows:

$$V'(z)=H_2(z)V(z) \qquad \text{(Equation 7)}$$

From the foregoing description it should be apparent that the enhancement $h_2$ to the spectral envelope 302 also can be added after the fixed codebook contribution is added to the adaptive codebook contribution. As FIG. 6 illustrates, the power spectrum envelope 302 can be enhanced by $h_2$ after the coefficients that characterize the excitation signal e(n) 106 are summed. It should also be apparent that the invention is not limited to a particular coding technology. Any perceptual coding technology can be used including a Code Excited Linear Prediction System (CELP) and an Algebraic Code Excited Linear Prediction System (ACELP).

The invention seamlessly provides an efficient coding system that improves the encoding and the decoding of perceptually important features of speech signals. The short-term enhancement need not be limited to a post processing application. Preferably, the short-term enhancement is integrated within or is a unitary part of an encoder related to a closed-loop search and a decoder as illustrated in FIGS. 8 and 9.

Figure 8:
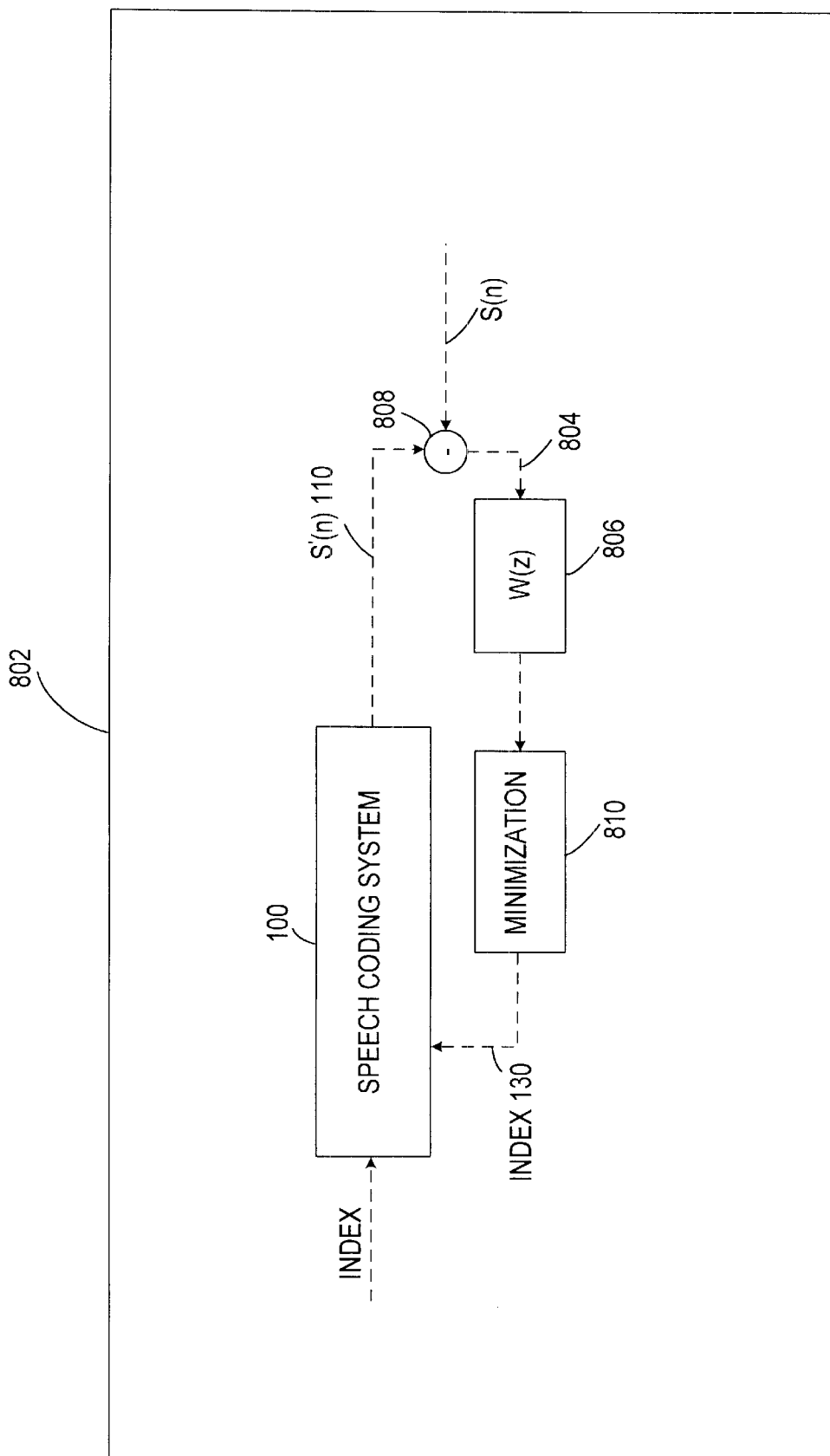
FIG. 8 is a block diagram of an alternative speech coding system implemented in an encoder.

Referring to FIG. 8, the fixed codebook contribution v(n) 120 shown in FIG. 1 an encoder 802 can be obtained in a closed loop. Optimization of a closed-loop prediction is accomplished by minimizing the power of a closed loop residual signal é(n) 804 defined by s'(n)–s(n). Preferably, the closed loop residual signal é(n) 804 is filtered by a weighting function such as a tunable perceptual weighting filter W(z) 806 or a pole-zero filter.

To illustrate the operation of a closed-loop embodiment of the encoder 802, FIG. 8 shows the reconstructed speech signal s'(n) 110 subtracted from the speech signal s(n) by a subtracting circuit 808. The difference, which is preferably the closed loop residual signal é(n) 804, is filtered by the weighting filter W(z) 806. The filtered closed loop residual signal é(n) 804 is conditioned by a minimizing circuit 810, which derives the fixed codebook index 130. Preferably, the minimizing circuit 810 comprises software and/or hardware that minimize the closed loop residual signal é(n) 804 through a closed loop search of the fixed codebook index 130. In alternative embodiments, the closed-loop selection of the fixed codebook index 130 is repeated until a desired reconstructed speech signal s'(n) 110 resolution is attained.

Figure 9:
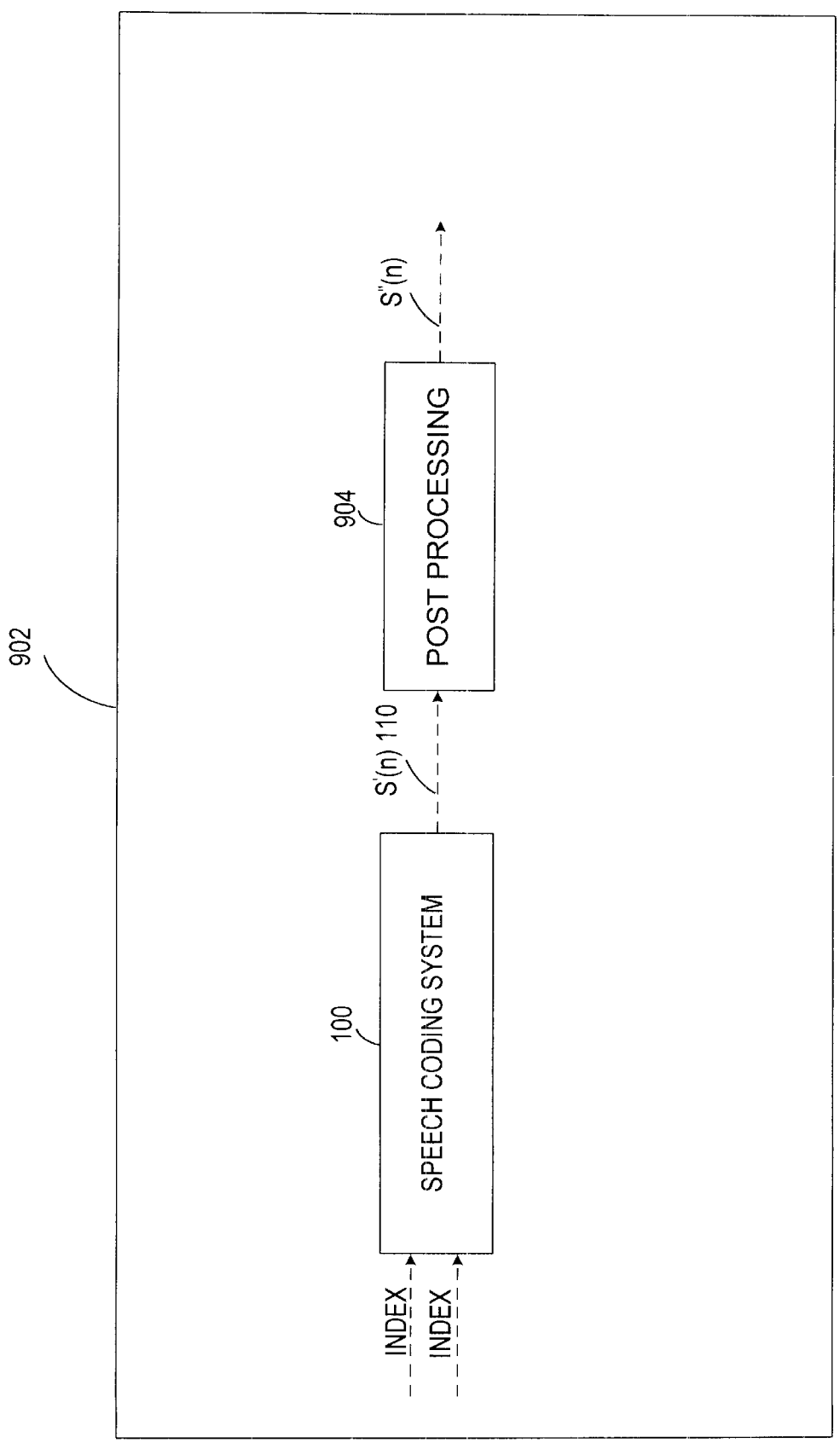
FIG. 9 is a block diagram of an alternative speech coding system implemented in a decoder.

In the decoder 902 illustrated in FIG. 9, a post enhancement function may be implemented to filter and condition the reconstructed speech signal s'(n) 110. In this embodiment, a post processing 904 conditions the reconstructed speech signal s'(n) 110 by sharpening the formants' 306 bandwidths. Preferably, the post processing 904 minimizes the noise that may lie within the spectral valleys between the formants 306 by emphasizing the formants' bandwidths.

While various embodiments of the invention have been described, it will be apparent to those of ordinary skill in the art that many more embodiments and implementations are possible that are within the scope of this invention. Accordingly, the invention is not to be restricted except in light of the attached claims and their equivalents.

What is claimed is:

1. A speech communication system comprising:
   an adaptive codebook that characterizes a speech segment;
   a fixed codebook that characterizes the speech segment and generates an excitation, wherein said excitation is scaled by an adaptive factor to generate a scaled signal;
   a filter configured to filter the scaled signal by an enhancement that emphasizes the formants of a Linear Prediction Coding spectrum to generate a filtered signal;
   a summer configured to sum the filtered signal with an output of the adaptive codebook to generate a summed signal;
   a convolver configured to convolve the summed signal to generate a convoluted signal; and
   a synthesizer configured to filter the convoluted signal.

2. The system of claim 1, wherein the convolver comprises a spectral filter having a transfer function of $1/A(z/\alpha)$.

3. The system of claim 1, wherein the system comprises an extended Code Excited Linear Prediction System.

4. The system of claim 1, wherein the convolver emphasizes the formant structure convolving two time domain signals.

5. A speech communication system comprising:
   an excitation that characterizes a speech segment;
   a convolver having an input configured to receive the excitation; and
   a synthesizer coupled to an output of the convolver, the convolver being configured to emphasize a formant structure of a spectral envelope of the speech segment in a closed-loop of an encoder;
   wherein the convolver comprises a spectral filter configured to modify an input signal by a transfer function of the form $1/A(z/\alpha)$.

6. The system of claim 5 wherein the excitation is derived from an output of a first codebook and a second codebook.

7. The system of claim 6 wherein the first codebook comprises an adaptive codebook.

8. The system of claim 7 wherein the second codebook comprises a fixed codebook.

9. The system of claim 8 further comprising a minimizing circuit coupled to the fixed codebook.

10. The system of claim 9 further comprising a weighting filter coupled to the minimizing circuit.

11. The system of claim 10 further comprising a subtracting circuit coupled to the synthesizer and the weighting filter.

12. The system of claim 6 wherein the convolver generates a convoluted result of an enhancement signal and at least an output signal of the second codebook.

13. The system of claim 5 wherein the convolver is electrically coupled to an output of a summing circuit.

14. The system of claim 5 wherein the system comprises a Code Excited Linear Prediction System.

15. The system of claim 5 wherein the system comprises an eXtended Code Excited Linear Prediction System.

16. The system of claim 5 wherein the convolver comprises a short-term enhancement circuit configured to enhance at least one of the formants of the spectral envelope.

17. The system of claim 5 wherein the convolver comprises a short-term enhancement circuit configured to enhance the formant structure of the spectral envelope.

18. The system of claim 1 wherein $\alpha$ is less than about 0.1.

19. The system of claim 5 wherein the convolver is configured to emphasize the formant structure of the spectral envelope of the speech segment in a decoder.

20. A speech communication system comprising:
    a fixed codebook that characterizes a speech segment;
    an adaptive codebook that characterizes the speech segment;
    means for emphasizing a formant structure of an envelope of the speech segment connected to an output of the fixed codebook; and
    a synthesizer connected to an output of the means for emphasizing;
    wherein the means for emphasizing emphasizes the formant structure by convolving two time domain signals.

21. The system of claim 20 wherein the means for emphasizing comprises a filter.

22. The system of claim 20 wherein the means for emphasizing comprises a convolver.

23. The system of claim 20 wherein the means for emphasizing is connected to an output of a summing circuit.

24. A method that improves speech coding comprising:
    generating a fixed codebook index to select an excitation;
    scaling the excitation by an adaptive factor; and
    filtering the scaled excitation by an enhancement that emphasizes the formants of a Linear Prediction Coding spectrum in a closed-loop of an encoder;
    summing the filtered and scaled excitation with an output of an adaptive codebook; and
    convolving the summed signal and filtering the convoluted signal by a synthesizing filter.

25. The method of claim 24 wherein the act of filtering comprises a device having a transfer function of the form $1/A(z/\alpha)$.

26. The method of claim 25 wherein $\alpha$ is less than about 0.1.

27. The method of claim 24 wherein the filtering of the scaled excitation by the enhancement that emphasizes the formants of the Linear Prediction Coding spectrum occurs in a decoder.

28. The method of claim 24 wherein the fixed codebook index is derived by subtracting a reconstructed speech signal from a speech signal; filtering the difference between the reconstructed speech signal and the speech signal through a weighting function; and minimizing the filtered difference.

29. A speech coding method comprising:
    generating a fixed codebook index to select an excitation;
    convolving the excitation by an enhancement that emphasizes the formants of a Linear Prediction Coding spectrum;
    scaling the convolved excitation by an adaptive factor;
    summing the scaled and convolved excitation with an output of an adaptive codebook; and
    synthesizing the summed signal by a synthesizing filter.

30. The method of claim 29, wherein the convolving uses a spectral filter configured to modify an input signal by a transfer function of the form $1/A(z/\alpha)$.

31. The method oil claim 29, wherein the method is performed in an eXtended Code Excited Linear Prediction system.

32. The method of claim 29, wherein the convolving emphasizes the formant structure by convolving two time domain signals.

* * * * *